(12) United States Patent
Yasuda

(10) Patent No.: US 10,325,674 B2
(45) Date of Patent: Jun. 18, 2019

(54) APPARATUS, METHOD, AND SYSTEM FOR CREATING PHYLOGENETIC TREE

(71) Applicant: Hitachi, Ltd., Chiyoda-ku, Tokyo (JP)

(72) Inventor: Tomohiro Yasuda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 392 days.

(21) Appl. No.: 15/072,671

(22) Filed: Mar. 17, 2016

(65) Prior Publication Data
US 2016/0357902 A1 Dec. 8, 2016

(30) Foreign Application Priority Data
Jun. 3, 2015 (JP) .................................. 2015-113297

(51) Int. Cl.
*G01N 33/48* (2006.01)
*G01N 33/50* (2006.01)
*G16B 10/00* (2019.01)
*G16B 99/00* (2019.01)

(52) U.S. Cl.
CPC .............. *G16B 10/00* (2019.02); *G16B 99/00* (2019.02)

(58) Field of Classification Search
None
See application file for complete search history.

(56) References Cited

U.S. PATENT DOCUMENTS

| 6,718,305 | B1 | 4/2004 | Haeb-Umbach | |
|---|---|---|---|---|
| 2005/0136480 | A1* | 6/2005 | Brahmachari | G06F 19/24 435/7.1 |
| 2007/0259363 | A1* | 11/2007 | Amri | G06F 19/24 435/6.14 |
| 2008/0044839 | A1* | 2/2008 | Chinnaiyan | C07K 14/4748 435/7.1 |

(Continued)

FOREIGN PATENT DOCUMENTS

JP 2000-298495 A 10/2000

OTHER PUBLICATIONS

Landau et al. Clonal evolution in hematological malignancies and therapeutic implications. Leukemia, vol. 28, Oct. 1, 2013, pp. 34-43.*

(Continued)

*Primary Examiner* — Russell S Negin
(74) *Attorney, Agent, or Firm* — Crowell & Moring LLP

(57) ABSTRACT

According to the present invention, a phylogenetic tree can be created on the basis of frequency data regarding a large number of mutations detected from the samples of a cancer. Each sample to be analyzed contains a mixture of plural clones having different genomes. Mutations having about the same frequencies are grouped to make plural groups, and an analysis is executed based on data listing the mutation frequencies of individual groups (called mutation group frequency data). It is assumed that pairs of clones corresponding respectively to mutation groups such that frequencies of one group is equal to or greater than that of another (Continued)

in all the samples have parent-child relations, and a graph structure having the clones as vertices and the parent-child relations as edges is created. In this graph, parent-child relations contradictory to the mutation group frequency data are removed, and a clone to become a parent is selected in consideration of correlation coefficients among the mutation group frequencies in the samples.

10 Claims, 13 Drawing Sheets

Specification includes a Sequence Listing.

(56) References Cited

U.S. PATENT DOCUMENTS

2008/0077607 A1* 3/2008 Gatawood ........... H03M 7/3084

OTHER PUBLICATIONS

Jiao, W., et al., "Inferring clonal evolution of tumors from single nucleotide somatic mutations", BMC Bioinformatics, 2014, 15:35, pp. 1-16 (Sixteen (16) pages).
Zare, H., et al., "Inferring Clonal Composition from Multiple Sections of a Breast Cancer", PLoS Computational Biology, 2014, vol. 10, Issue 7, e10003703, pp. 1-15 (Fifteen (15) pages).
Friedman, N., et al., "A Structural EM Algorithm for Phylogenetic Inference", Journal of Computational Biology, 2002, vol. 9, No. 2, pp. 331-353 (Twenty-three (23) pages).

* cited by examiner

| PAIR OF MUTATIONS | EVIDENCE | RELIABILITY |
|---|---|---|
| MUTATION 217, MUTATION 912 | FLUORESCENCE HYBRIDIZATION | 1 |
| MUTATION 159, MUTATION 682 | SAME SEQUENCE | 0.85 |
| MUTATION 573, MUTATION 612 | FLUORESCENCE HYBRIDIZATION | 0.33 |
| MUTATION 627, MUTATION 801 | SAME SEQUENCE | 0.26 |
| MUTATION 553, MUTATION 987 | FLUORESCENCE HYBRIDIZATION | 1 |

|  | SAMPLE 1 | SAMPLE 2 | SAMPLE 3 |
|---|---|---|---|
| MUTATION GROUP 1 | 60% | 90% | 90% |
| MUTATION GROUP 2 | 40% | 30% | 20% |
| MUTATION GROUP 3 | 0% | 40% | 0% |
| MUTATION GROUP 4 | 30% | 20% | 20% |
| MUTATION GROUP 5 | 25% | 10% | 10% |
| MUTATION GROUP 6 | 25% | 20% | 70% |
| MUTATION GROUP 7 | 25% | 20% | 60% |

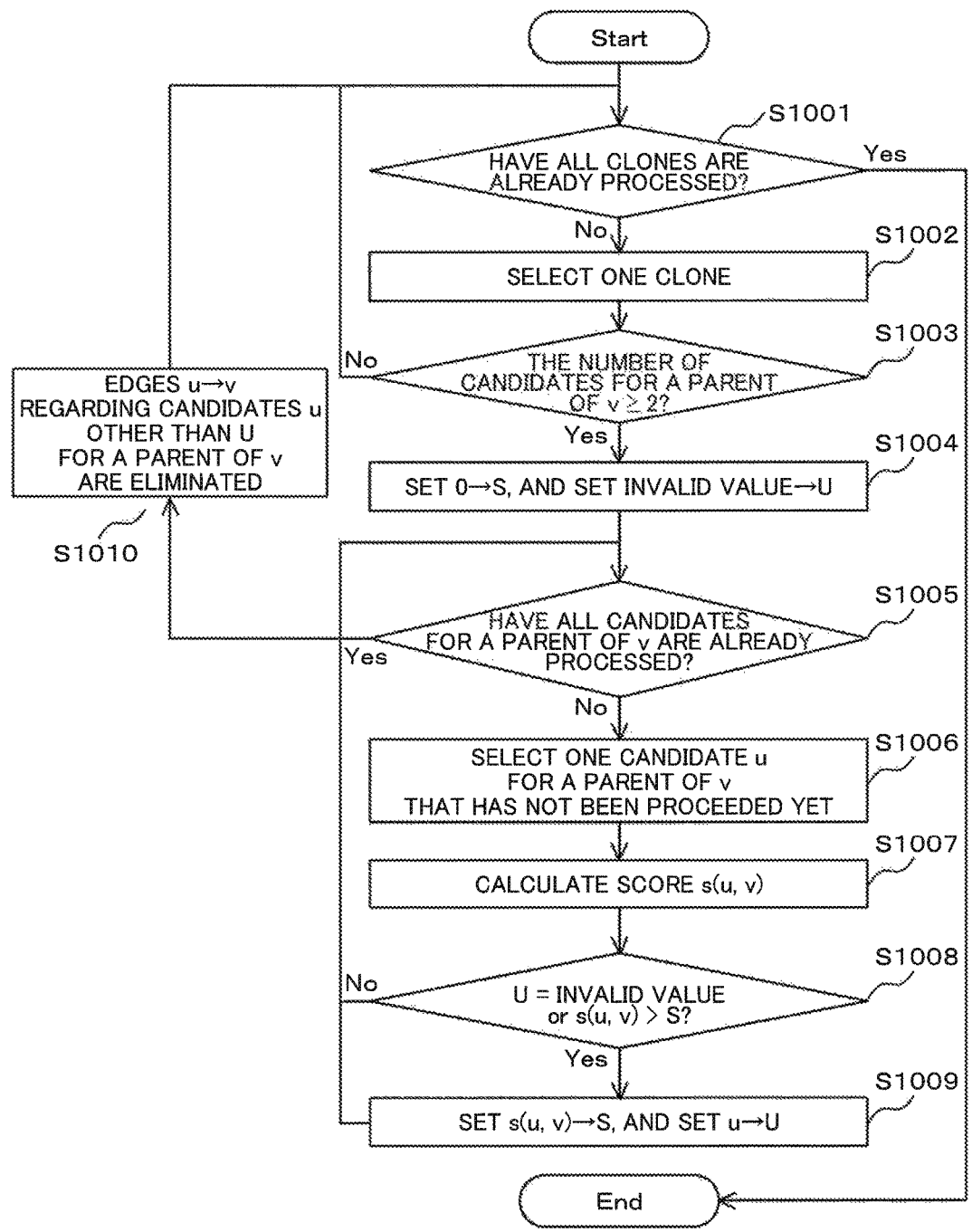
F I G. 1 0

F I G. 1 2
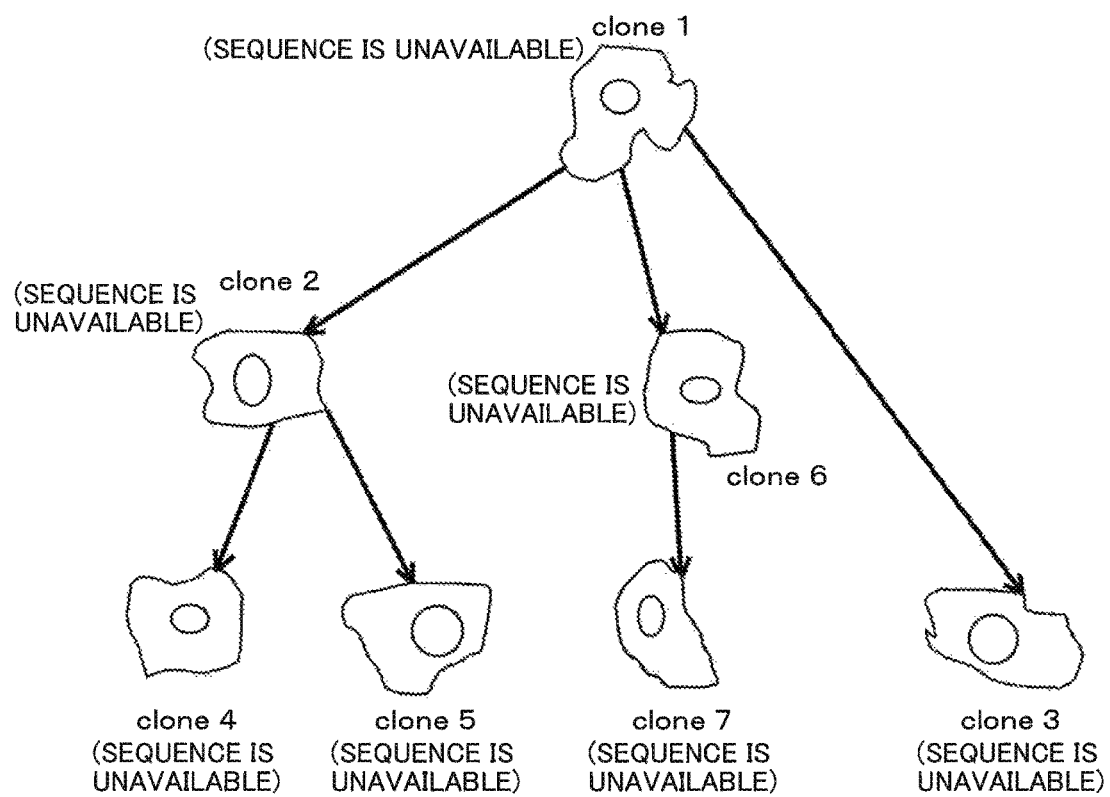

APPARATUS, METHOD, AND SYSTEM FOR CREATING PHYLOGENETIC TREE

INCORPORATION OF SEQUENCE LISTING

This application contains a Sequence Listing which has been submitted in ASCII format electronically via EFS-Web. This Sequence Listing in ASCII format, created on Apr. 18, 2016, is named SE0822US-Sequence_ST25.txt, is 904 bytes in size, serves as both the paper copy and the computer readable form of the Sequence Listing, and is hereby incorporated by reference in its entirety.

BACKGROUND OF THE INVENTION

The present invention relates to apparatuses, methods, and systems for creating phylogenetic trees, especially to an apparatus, a method, and a system suitable for creating a phylogenetic tree for cancer clones.

DNA sequencing with a next generation sequencer (Next Generation Sequencing: NGS) makes it possible that a genome can be sequenced at drastically low cost than by the conventional Sanger method. The cost of genome sequencing, which was about one hundred million U.S. dollars in 2001, was lowered to 4,905 U.S. dollars in 2014 thanks to next generation sequencers. Not only the cost of genome sequencing is lowered, but also vast amounts of sequence data can be obtained in a short period, and an apparatus that can generate vast amounts of sequence data exceeding one trillion bases at a time has been also produced. Such a technology makes it possible that a genome can be sequenced on the basis of samples obtained from a cancer patient.

A problem in the case of executing genome sequence analysis on samples obtained from cancer cells of a patient is the fact that samples of cancer cells form a mixed aggregation comprised of plural kinds of cancer cells, which have mutations at different positions of their genomes, and normal cells. Such nonuniformity among samples is referred to as heterogeneity. Hereinafter, an aggregation of cells whose genomes are almost the same will be referred to as a clone. A sample of a cancer is a mixture of normal cells and plural clones generated from mutations of genomes.

In the case of a mixed aggregation, it cannot be directly judged whether mutations which are detected at different positions are derived from the same cell or not except for the case of mutations detected at positions on the genomes very near to each other. Therefore, it is difficult to investigate how mutations have effects on the functions of the cell. However, in recent years, a technology is proposed in which, among mutations detected in samples of cancers on the basis of the number of NGS sequences having mutations, mutations having almost equal ratios of being included in the cells in the samples are grouped, and the group is identified in association with the frequency of the group (referred to as a mutation group frequency, hereinafter) (Refer to FIG. 2 shown in "Zare et al., PLoS Comput Biol 2014, 10(7): e1003703").

If it is assumed that a mutation group and the corresponding mutation group frequency are accurately predicted, and that there are no other mutation groups whose mutation group frequencies are completely the same as that of the mutation group through all the samples, the mutation group can be associated with a clone one-to-one. In other words, each mutation group is associated with a clone in which a mutation belonging to the group is first generated, and its mutation group frequency is equal to a summation of the mixture ratio of the clone and the mixture ratios of clones that are derived and evolve from the clone. If not only a mutation group and its frequency, but also evolutionary relations among clones, that is to say, changing processes that show in which clones mutations are generated and into which clones the clones change can be presumed, it can be expected that an important clue to identifying a mutation, which plays an important role in the advancing process of a cancer, is obtained.

"Jiao et al. 2014, BMC Bioinformatics 15:35" (nonpatent literature 1) discloses a technology for creating a phylogenetic tree on the basis of samples of cancers. In the technology disclosed in the above nonpatent literature 1, among NGS sequences obtained from samples of cancers, the number of sequences having mutations in the positions of the mutations on genomes and the number of sequences having no mutations are input. Mixture ratios and phylogenetic trees of clones are presumed and evaluated on the basis of the inputs, and at the same time a mixture ratio and a phylogenetic tree of a clone that are most matched with the given inputs is calculated.

In addition, as a related technology for creating a tree structure using correlation coefficients, a technology disclosed in Japanese Patent Application Laid-Open No. 2000-298495 is well-known.

SUMMARY OF THE INVENTION

An evolutionary neighborhood among plural species or an evolutionary near relation among the same species such as among people in plural regions is represented by a dendritic diagram such as an example shown in FIG. 14. This diagram is referred to as a phylogenetic tree. In general, species and the like that are targets for which a phylogenetic tree is created is referred to as OTU's (operational taxonomy units). OTU's are disposed at the ends of a phylogenetic tree, and the length of an edge of the phylogenetic tree represents an evolutionary distance. Next, the shapes and the lengths of edges of a phylogenetic tree that are highly matched with the given DNA sequences 301 are calculated (Refer to "Friedman at al. 2009, J Comput Biol. 9(2):331-53"). By creating the phylogenetic tree, species which are near to each other are explicitly shown.

As shown by the example in FIG. 14, a phylogenetic tree based on DNA sequences are created under the assumption that the DNA sequences 301 of individual OTU's has respectively been determined, and that the mutations that the individual OTU's have are given as inputs.

In reality, in the case where a phylogenetic tree is created on the basis of samples of a cancer of a certain patient, the samples of the patient generally form a mixed aggregation comprised of plural kinds of cancer cells, which have mutations at different positions of their genomes, and normal cells, and sequencing is executed while individual clones remain mixed with each other without being isolated. Furthermore, the length of each NGS sequence is equal to only about the length of a few hundred bases. Therefore, even if the DNA sequences of a small region including mutations can be obtained, the DNA sequences of the whole genomes are unavailable and from which clones the mutations are derived is also unavailable. As a result, such a related technique as shown by the example in FIG. 14, which is executed under the assumption that the DNA sequences 301 of the OUT's are given, cannot be used.

The technique disclosed in the nonpatent literature 1 is executed under the assumption that a large amounts of sequences, each of which has a mutation, can be obtained in the samples, and that these sequences can be used. Therefore, it is assumed that the ratio of cells that have each mutation can be very accurately calculated. However, since it is difficult to obtain such data regarding a large number of mutations, it becomes necessary to obtain data regarding mutations which were narrowed down in advance. In addition, it is difficult for the calculation technique, which is disclosed in the nonpatent literature 1 and used for calculating the mixture ratios of clones and the evaluation value of a phylogenetic tree, to accurately reflect a large number of mutations in its calculation results. In contrast, although information about a large number of mutations can be obtained in the case of data obtained by exhaustive sequence analysis, it becomes expensive to get data about individual mutations with accuracy required by the above-mentioned technique. Therefore, it is difficult to apply the above-mentioned technique to the data obtained by exhaustive sequence analysis.

In contrast, Japanese Patent Application Laid-Open No. 2000-298495 discloses a technology in which a tree structure is created using only correlation coefficients. However, in the case where a phylogenetic tree is created using only correlation coefficients on the basis of frequencies obtained from cancer samples of a patient which are mixed aggregations of plural types of cancer cell whose DNA sequence are unknown and normal cells, it is expected that only a phylogenetic tree with low accuracy that cannot exist in reality is created.

One of the objects of the present invention is to provide an apparatus, a method, or a system that is capable of providing a highly accurate phylogenetic tree regarding plural clones that are identified in samples of a cancer.

A typical aspect of the present invention is as follows. A phylogenetic tree creation apparatus includes a graph creation section, a parent-child relation determination section, and an input section for inputting mutation group frequency data, wherein, in the case where there are plural samples that contain mixture of plural clones having different genomes, mutations having about the same frequencies are grouped into one group to make plural groups, and data listing the frequencies of individual groups is referred to as the mutation group frequency data. The graph creation section creates a parent-child graph in which the clones are set to vertices and candidates for parent-child relations are set to edges on the basis of the mutation group frequency data; and the parent-child relation determination section selects clones to become parents of the clones in consideration of correlation coefficients showing correlations among the mutation group frequencies in the plurality of samples, and creates a phylogenetic tree for the plurality of clones.

According to one aspect of the present invention, a phylogenetic tree for clones can be created highly accurately and at low cost on the basis of frequency data that contain many mutations detected in samples of a cancer.

BRIEF DESCRIPTION OF THE DRAWINGS

FIG. 10 is a diagram showing an example of the processing flowchart of the parent-child relation determination section 111 shown in FIG. 1;

FIG. 12 is a diagram showing an example of a phylogenetic tree for clones generated in the first embodiment;

FIG. 14 is a diagram showing a phylogenetic tree created from already-determined DNA sequences using a related technology.

DETAILED DESCRIPTION OF THE PREFERRED EMBODIMENTS

Hereinafter, one embodiment of the present invention will be described in detail with reference to the accompanying drawings. An embodiment that is preferable for creating a phylogenetic tree representing evolutionary relations among clones will be described on the basis of the mixture ratios of clones and the like.

First Embodiment

Figure 1:
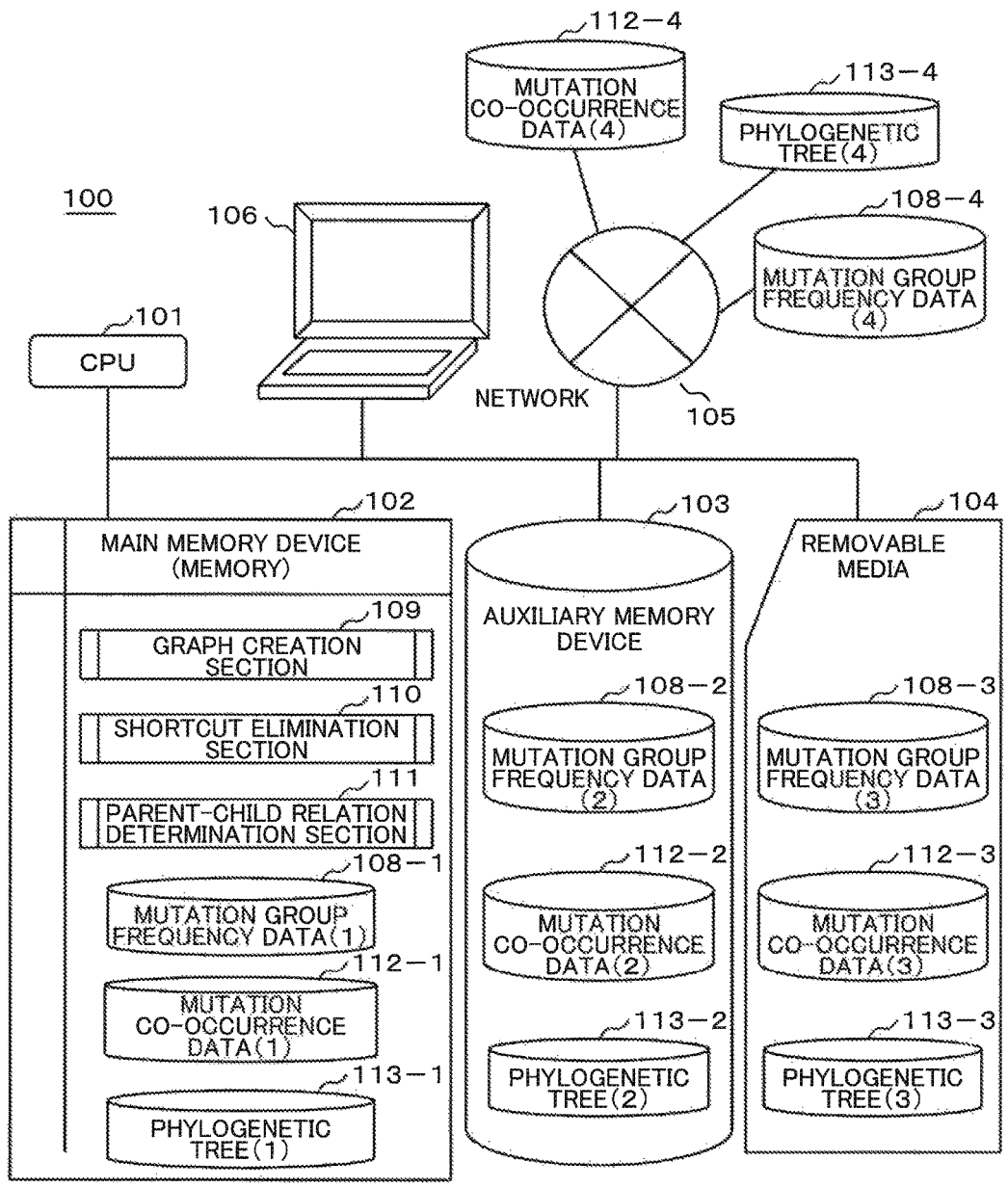
FIG. 1 is a diagram showing a configuration example of a phylogenetic tree creation apparatus for clones according to a first embodiment of the present invention.

FIG. 1 is a diagram showing a configuration example of a phylogenetic tree creation apparatus 100 according to a first embodiment of the present invention. The phylogenetic tree creation apparatus 100 includes a CPU (Central Processing Unit) 101; a memory section (main memory device (memory)) 102, an auxiliary memory device 103, a removable medium 104); a user interface unit 106; a communication control unit (not shown); and the like. This phylogenetic tree creation apparatus 100 is coupled with external networks via a network 105 such as a LAN (Local Area Network). The main memory device 102 stores various types of program executed by the CPU 101 and various types of data necessary for the CPU 101 to execute these programs. The main memory device 102 includes at least a memory such as a RAM (Random Access Memory) that stores programs that are executed the CPU 101 so that these programs function as a graph creation section 109, a shortcut elimination section 110, and a parent-child relation determination section 111. The main memory device 102 can also record mutation group frequency data 108-1, mutation co-occurrence data 112-1, and phylogenetic tree 113-1 regarding samples of cancer cells. Here, the phylogenetic tree creation apparatus 100 can be configured in such a way that parts or entireties of the graph creation section 109, the shortcut elimination section 110, and the parent-child relation determination section 111, which are realized by the above programs, are disposed on networks. In other words, the phylogenetic tree creation apparatus 100 can be configured to include so-called cloud computing.

The auxiliary memory device 103 is a memory device such as an HOD (Hard Disk Drive) that can record mutation group frequency data 108-2 and the like. The removable medium 104 is a memory device that can be easily put on and taken off the phylogenetic tree creation apparatus 100 such as a CD or DVD that can record mutation group frequency data 108-3 or the like. The phylogenetic tree creation apparatus can be also configured to be able to access a storage device, which is coupled to the network 105 and stores mutation group frequency data 108-4, mutation co-occurrence data 112-4, and phylogenetic tree 113-4, via the network 105. The user interface unit 106 is an input/output device that provides user interface such as a keyboard, a mouse, or a display. It is desirable that pieces of information about mutation group frequency data 108 and a parent-child graph (to be described later) should be displayed on the display, that is a type of user interface 106, or the like as outputs.

Individual data stored in the main memory device 102, the auxiliary memory device 103, the removable medium 104, and a storage device coupled to the network, for example, the mutation group frequency data (108-1 to 108-4) can have the same contents. These data can be stored as the mutation group frequency data (1) 108-1 in the main memory device 102 as needed in the case where the data is read or written by the CPU 101, and in the case where the power supply to the phylogenetic tree creation apparatus 100 is turned off, or in the case where the free space of the main memory device 102 is exhausted, the mutation group frequency data (1) 108-1 can be copied from the main memory device 102 to other devices. In addition, it is conceivable that the data are stored from other devices (not shown) to the mutation group frequency data (3) 108-3 in the removable medium 104 or to the mutation group frequency data (4) 108-4 in the external storage device in advance, and at the time of the start of processing, or at the time when the phylogenetic tree creation apparatus 100 starts to run or starts processing, the data are copied to the main memory device 102 or the auxiliary memory device 103 in the phylogenetic tree creation apparatus 100.

Furthermore, in descriptions that can be done regardless of the location of these data, it will be assumed that the mutation group frequency data 108, the mutation co-occurrence data 112, and the phylogenetic tree 113 are generically used.

Figure 2:
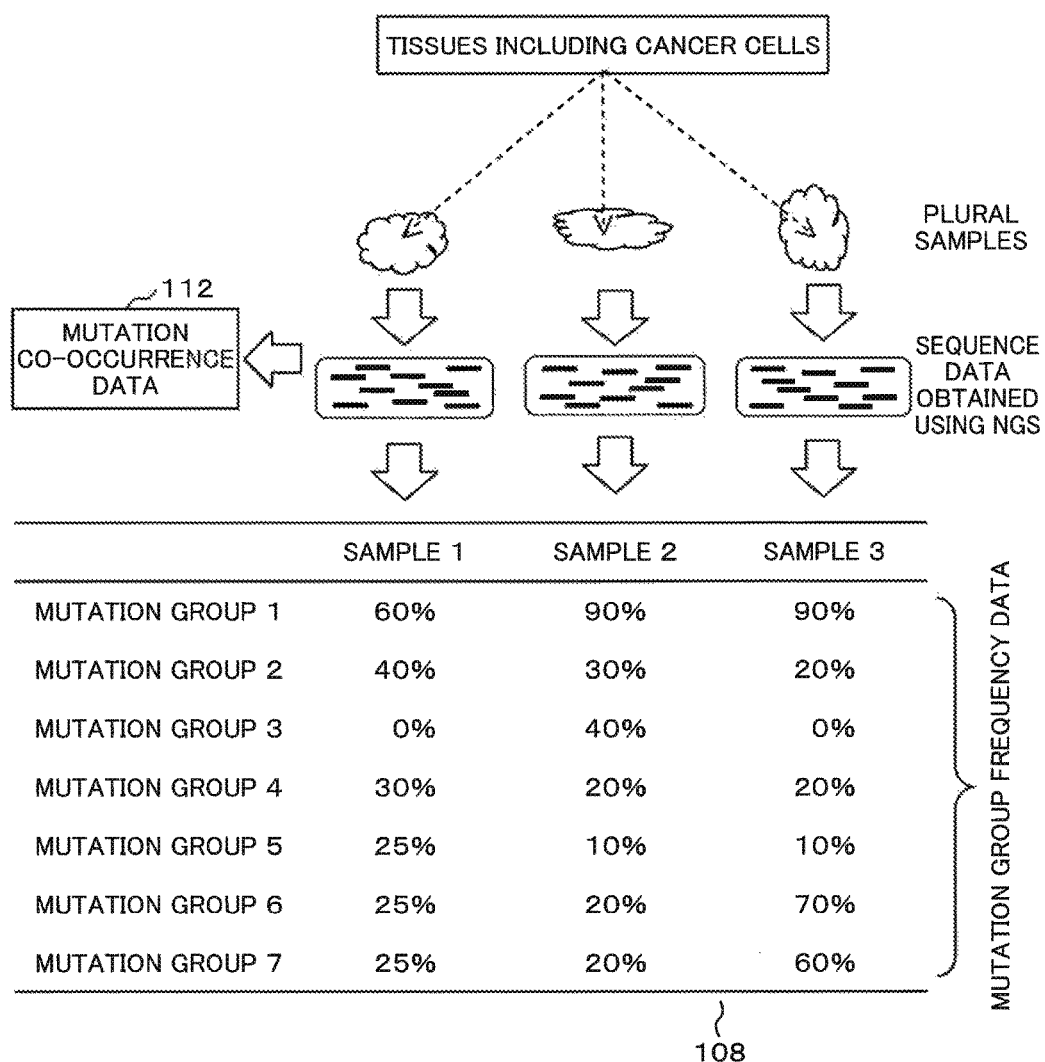
FIG. 2 is a diagram showing the outline of processing for calculating mutation group frequencies from NGS sequences.

FIG. 2 is a diagram showing the outline of processing for calculating mutation group frequencies from data of DNA sequences obtained using NGS on the basis of plural samples of tissues including cancer cells of a patient, for example, plural samples of tissues of the stomach of the patient. Plural clones having different genomes mixedly exist in plural samples. In other words, plural samples including cancer cells are mixtures of normal cells and plural clones generated from the mutations of genomes, and genome sequences of each clone in the samples are unavailable.

In each of samples of tissues including such cancer cells, groups each including almost equal number of mutations, and the ratio of cells having mutations in each group (mutation group frequency) are estimated, with the result that mutation group frequency data 108 is created. On the other hand, mutation co-occurrence data 112 is obtained from a part of plural samples of tissues including cancer cells using an experimental technique such as fluorescence hybridization. The mutation co-occurrence data 112 can be also obtained from sequence data obtained by analyzing the samples using NGS.

Figures 3, 4:
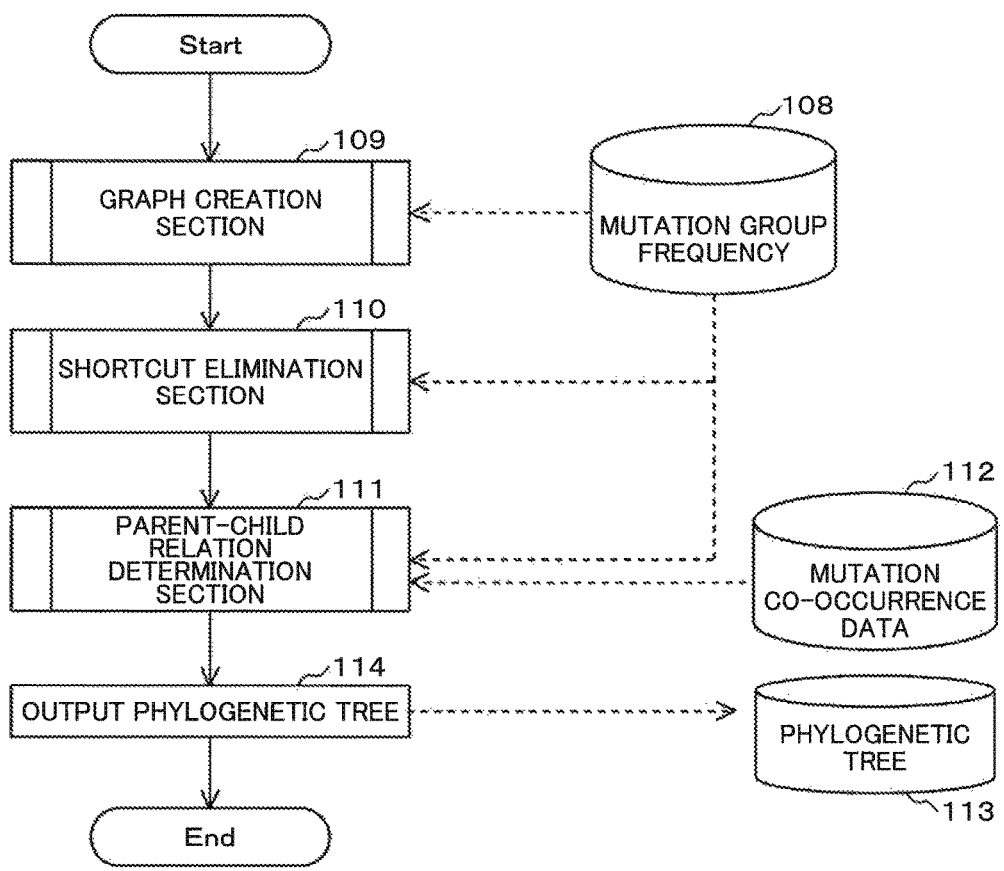
FIG. 3 is a diagram showing an example of mutation co-occurrence data shown in FIG. 1.
FIG. 4 is a diagram showing an example of a flowchart showing the outline of the processing of the first embodiment.

FIG. 3 shows an example of the mutation co occurrence data 112. The mutation co-occurrence data 112 is data in which a judgment whether a pair of mutations in samples of cancer cells, for example, a pair of a mutation 217 and a mutation 912, occurs in the same cell or not as well as the evidence (for example, fluorescence hybridization) for the judgment and reliability (for example, a value between 0 to 1) for the judgment is recorded.

Figure 5:
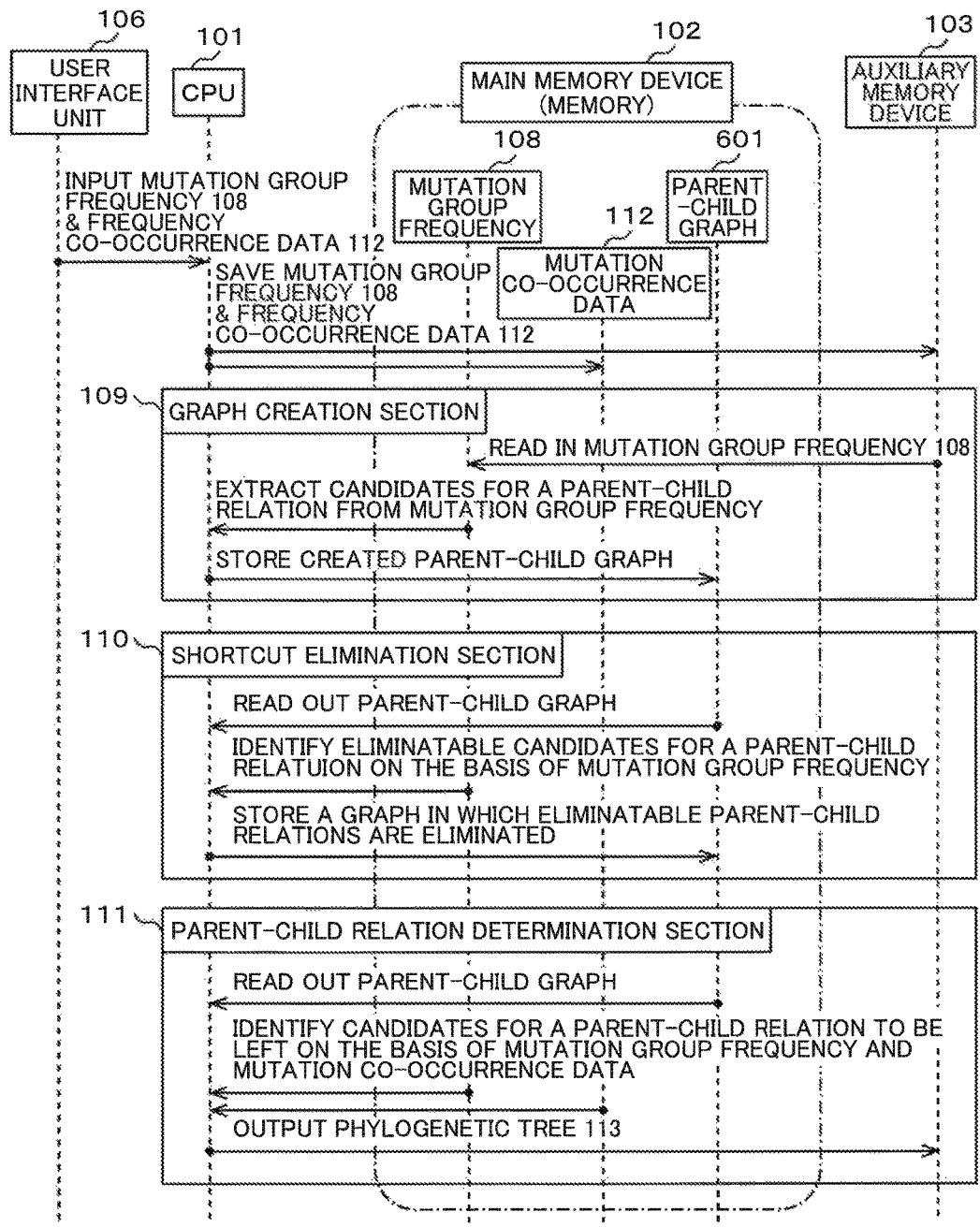
FIG. 5 is a diagram showing an example of the processing sequence of the first embodiment.
Figure 6:
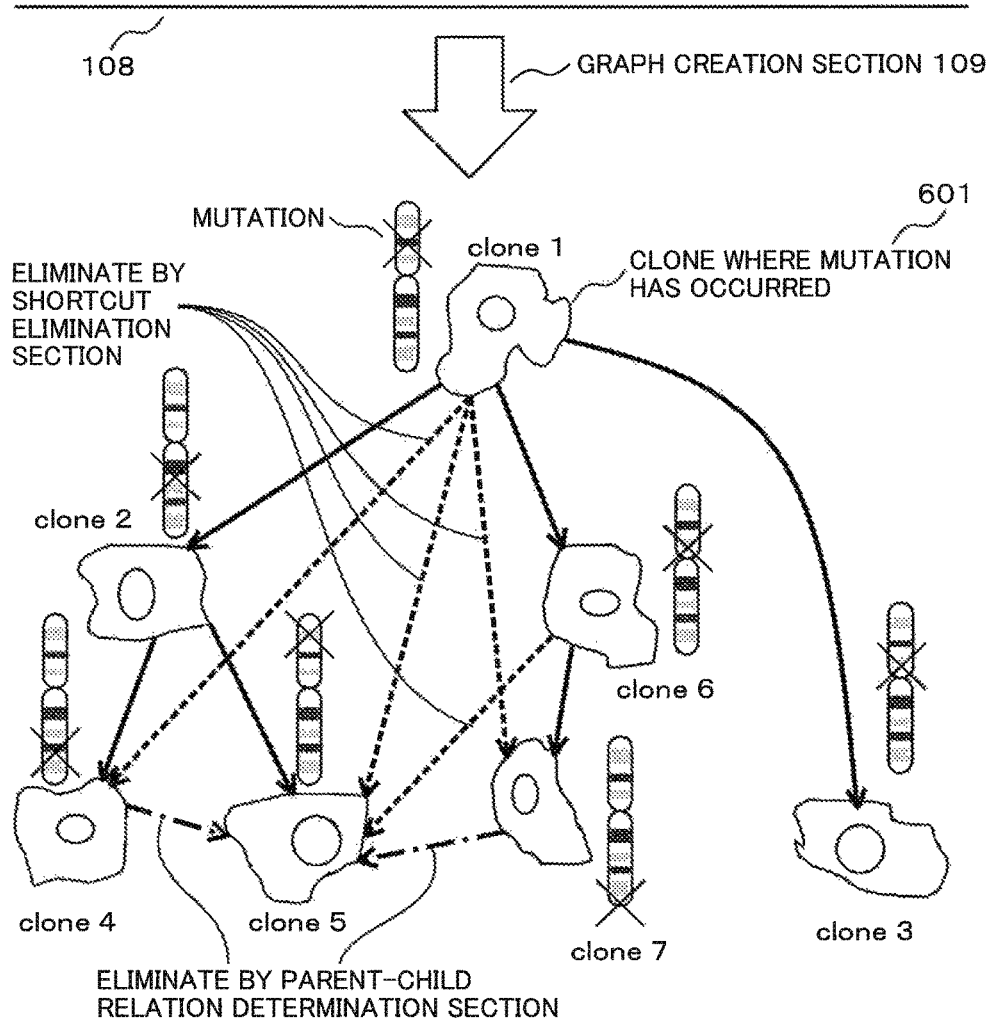
FIG. 6 is a diagram showing the outline of the flow of the processing for calculating a phylogenetic tree for clones from the mutation group frequencies in the first embodiment.

FIG. 4 is a diagram showing the outline of the processing for creating a phylogenetic tree 113 on the basis of mutation group frequency data 108 and mutation co-occurrence data 112 in the phylogenetic tree creation apparatus 100, and FIG. 5 is a diagram showing an example of a processing sequence in which individual processing sections of the phylogenetic tree creation apparatus 100 operate in cooperation with each other. Furthermore, FIG. 6 is a diagram showing the image of the flow of the entirety of the processing shown in FIG. 4. Individual pieces of processing will be explained with reference to these drawings.

(1) Creation of a Parent-Child Graph Using the Graph Creation Section 109

After mutation group frequency data 108 in samples of a cancer cell is read in, a pair of clones that have a possibility that they have a parent-child relation is identified using the graph creation section 109. In the case where, of any two clones, one clone is referred to as a clone u and the other is referred to as a clone v, a condition used for a judgment whether the clone u is a candidate for a parent of the clone v is that mutation frequencies corresponding to the clone u are larger than frequencies corresponding to the clone v in all samples. With the use of this judgment result, a graph structure is created.

For example, in a mutation group frequency data 108 shown in FIG. 6, the mutation group frequencies of a mutation group 1 are larger than the mutation group frequencies of a mutation group 2 and those of a mutation group 3 in all samples 1 to 3, therefore there is a possibility that the mutation group 1 has parent-child relations with the mutation group 2 and the mutation group 3. In other words, it can be estimated that a mutation occurred first in the mutation group 1. In addition, the mutation group frequencies of the mutation group 2 are larger than the mutation group frequencies of a mutation group 4 in all the samples 1 to 3, therefore there is a possibility that the mutation group 2 has a parent-child relation with the mutation group 4. In contrast, the mutation group 2 and the mutation group 3 in the samples 1 to 3 do not have a relation, "the mutation group frequencies of one mutation group are larger than the mutation group frequencies of the other mutation group in all samples", and therefore it is judged that there is no parent-child relation between these mutation groups.

In general, a graph structure is a data structure in which plural elements (referred to as vertices) are connected to each other via lines referred to as edges. The graph creation section 109 creates a graph by setting vertices to clones, and making edges between pairs of clones each of which is judged to be a candidate for a parent-child relation, where the direction of the edge is a direction from the parent to the child. Hereinafter, this graph will be referred to as a parent-child graph 601.

(2) Shortcut Elimination Section 110

Figure 7:
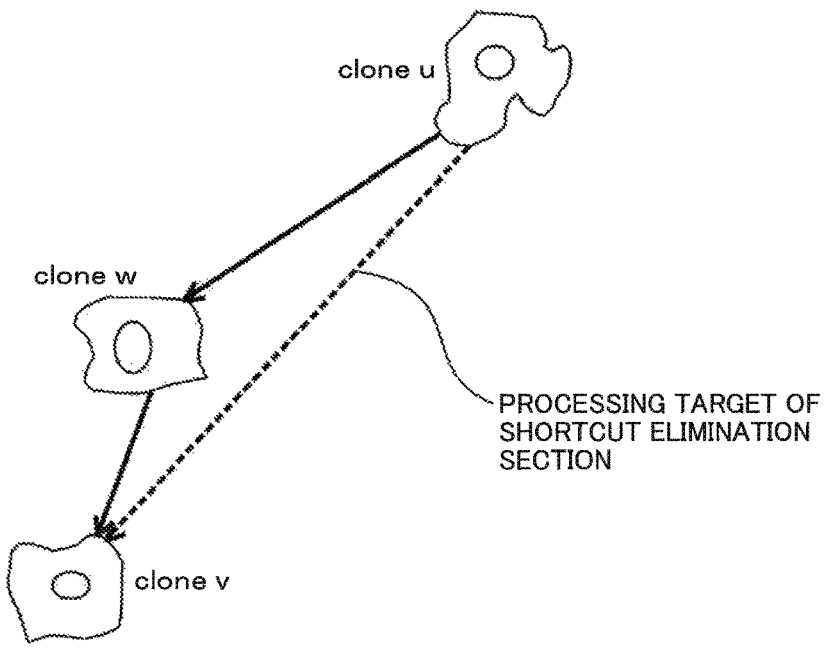
FIG. 7 is a diagram showing an example of the case where there are plural candidates in the process in which a certain clone evolves to become another clone.
Figure 8A:
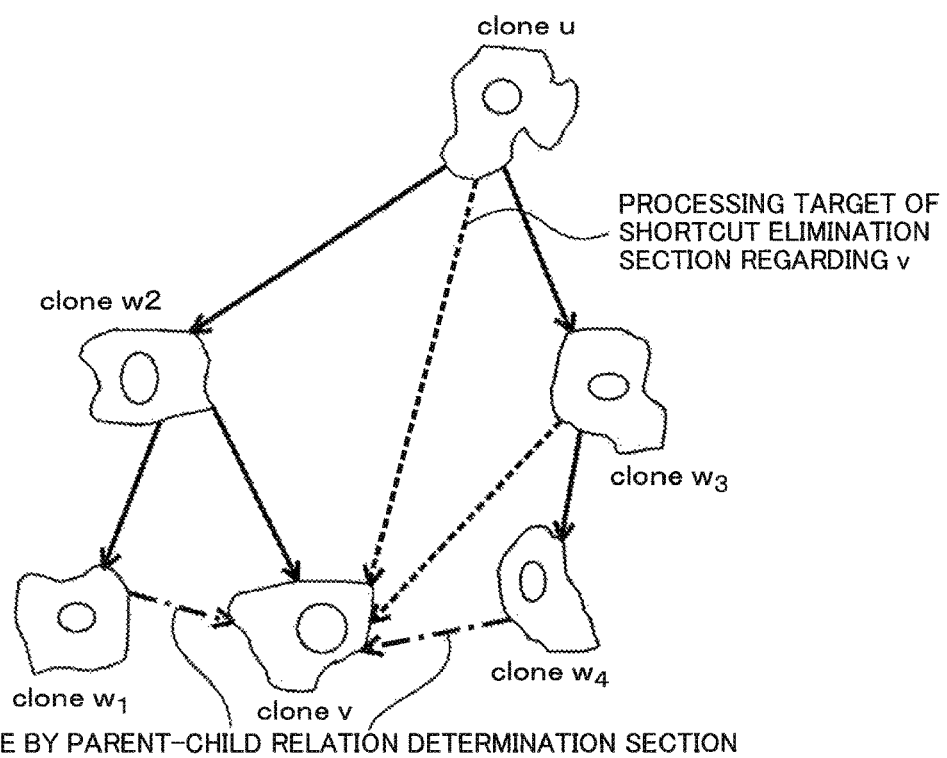
FIG. 8A is a diagram showing another example of the case where there are plural candidates in the process in which a certain clone evolves to become another clone.

Among edges that are present in a parent-child graph 601, edges that are contradictory to the mutation group frequency data 108 are removed. In a parent-child graph 601 shown in FIG. 6, an edge from a clone 1 to a clone 4, an edge from the clone 1 to a clone 5, an edge from the clone 1 to a clone 7, and an edge from a clone 6 to the clone 5 are eliminated by the shortcut elimination section 110. For example, in FIG. 7, an edge showing that there is a direct parent-child relation between a clone u and a clone v is contradictory to an evolutionary route from the clone u to the clone v via a clone w. In other words, when the mutation group frequency data 108 is referred to, in the sample 1, the frequencies of the mutation group 1 is smaller than the sum of the frequencies of the mutation group 2 and the mutation group 4, therefore a route from the clone 1 to the clone 4 is eliminated. Furthermore, in FIG. 8A, an edge showing that there is a direct parent-child relation between a clone u and a clone v is contradictory to evolutionary route from the clone u to the clone v via clones $w_1$, $w_2$, $w_3$, and $w_4$. If it is judged that a route from the clone u to the clone v have to pass any of these clones, an edge that shows there is a direct parent-child relation between the clone u and the clone v is eliminated. Details of shortcut elimination processing will be explained later with reference to FIG. 9. Here, although it is desirable that the phylogenetic tree creation apparatus 100 should include the processing function of the shortcut elimination section 110, this function can be omitted by enhancing the function of the parent-child relation determination section 111.

(3) Parent-Child Relation Determination Section 111

If there still remains a clone having plural candidates for its parent after applying the shortcut elimination section 110, a candidate that is most likely to be its parent is selected. The parent-child relation determination section 111 selects a clone that becomes a parent of each clone in consideration of correlation coefficients among mutation group frequencies in plural samples. Thanks to the above selection, the parent-child graph 601 is transformed into a phylogenetic tree 113. In the parent-child graph 601 shown in FIG. 6, an edge from the clone 4 to the clone 5 and an edge from the clone 7 to the clone 5 are eliminated by the parent-child relation determination section 111. The details will be described using FIG. 10.

Figure 8B:
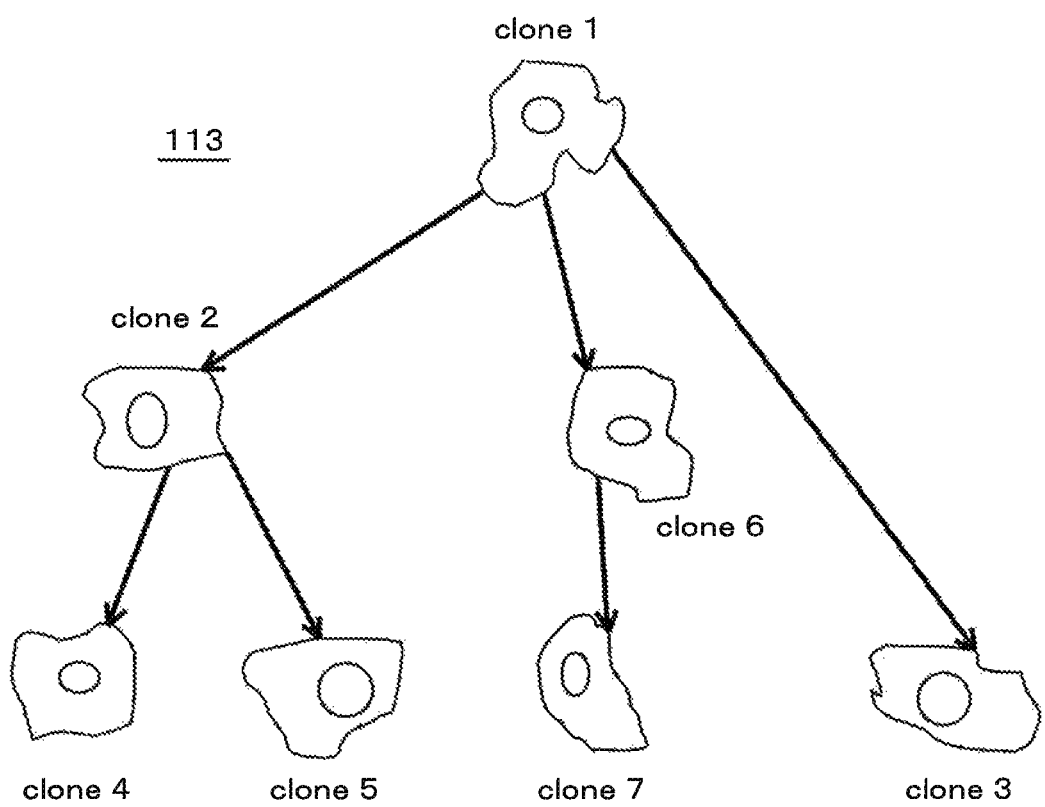
FIG. 8B is a diagram showing an example of phylogenetic tree generated by removing contradictory edges using a shortcut elimination section and a parent-child relation determination section.

FIG. 8B shows an example of phylogenetic tree 113 that is created after contradictory edges are eliminated by the shortcut elimination section 110 and the parent-child relation determination section 111.

Figure 9:
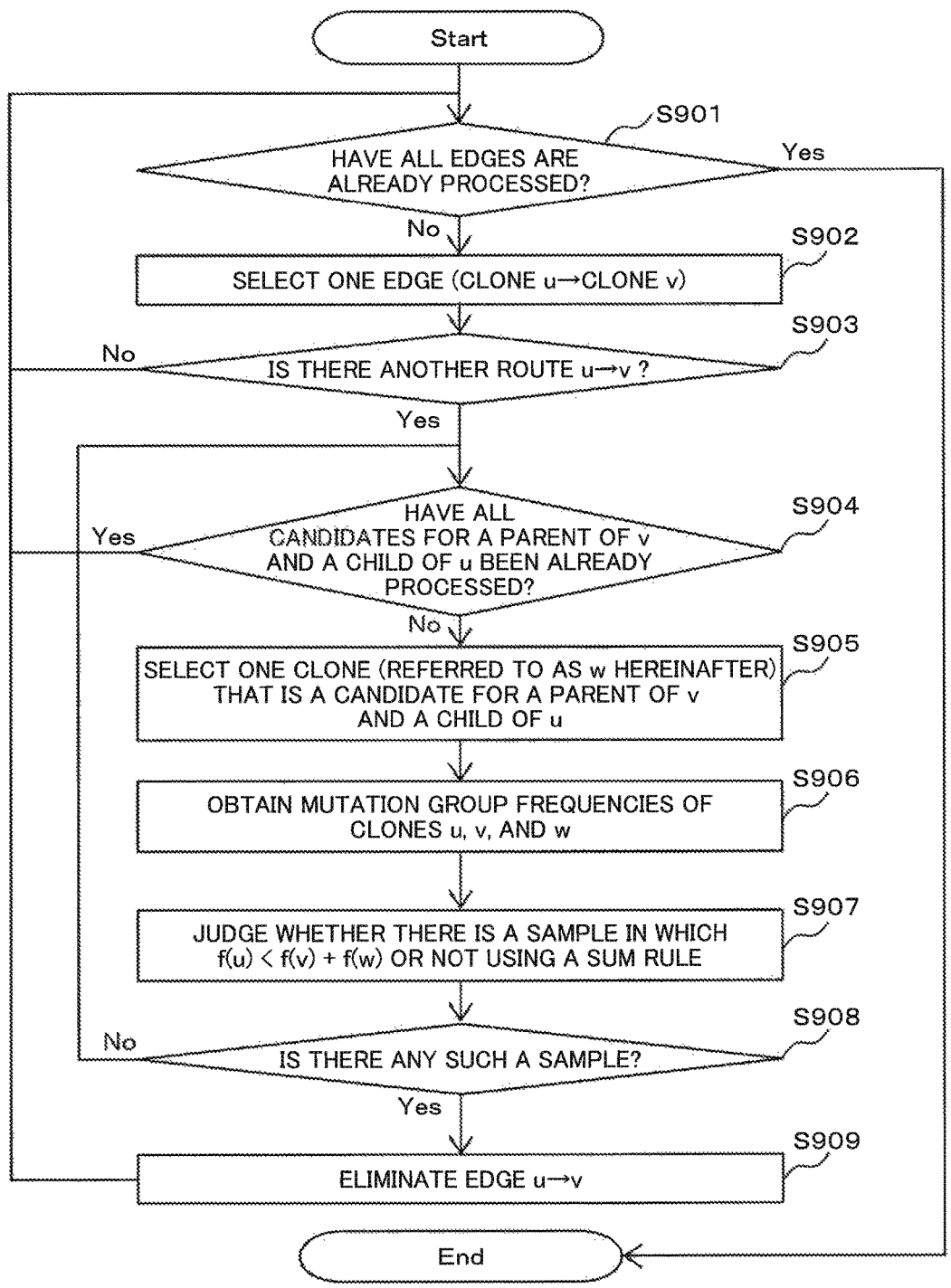
FIG. 9 is a diagram showing an example of the processing flowchart of the shortcut elimination section 110 shown in FIG. 1.

FIG. 9 is a diagram showing an example of the processing flowchart of the shortcut elimination section 110. The details of the shortcut elimination section will be described with reference to FIG. 9, FIG. 7, FIG. 8A, and FIG. 8B.

At step S901, the shortcut elimination section 110 is applied to all the edges of the parent-child graph 601. If pieces of processing to all, the edges have been finished, the whole processing is finished.

At step S902, one edge to become a processing target is selected. Hereinafter, it will be assumed that this edge extends from a clone u to a clone v.

At step S903, it is judged whether there is a route from the clone u to the clone v other than the edge selected at step S902 or not. If there is no such route, the edge from the clone u to the clone v is not eliminated. The flow goes back to step S901 to perform processing on another edge.

At step S904, pieces of processing at steps S904 to S908 are applied to every clone w (w≠u, and w≠v) that is a candidate for a parent of the clone v, and at the same time has the clone u as a candidate for a parent of its own. If such processing on every clone w has already been finished, the processing on edges from the clone u to the clone v is finished. The flow goes back to step S901 to perform processing on another edge.

At step S905, one clone w, which is a candidate for a parent of the clone v and has the clone u as a candidate for a parent of its own and which has not been processed yet, is selected.

At step S906, mutation group frequencies corresponding to individual clones u, v, and w are obtained from the mutation group frequency data 108 in order for these obtained frequencies to be used at a judgment at step S907.

At step S907, it is judged whether there is a possibility that there is not a parent-child relation or an ancestor-descendant relation between the clone v and the clone w using a sum rule (The sum rule is described in FIG. 1B in the nonpatent literature 1). In the case where mutation group frequencies corresponding to the clones u, v, and w are respectively represented by f(u), f(v), and f(w), and f(u)<f(w)+f(v) in any of samples, if w is not a parent of v, or w is not an ancestor of v, this is contradictory to data of the mutation group frequencies.

At step S908, if there is not any sample in which it is judged that f(u)<f(w)+f(v) at step S907, the flow goes back to step S904.

At step S909, if there is any sample in which it is judged that f(u)<f(w)+f(v) at step S907, the edge from the clone u to the clone v is eliminated, and the flow goes back to step S901.

FIG. 10 is a diagram showing an example of the processing flowchart of the parent-child relation determination section 111. The processing of the parent-child relation determination section will be described with reference to FIG. 8A and FIG. 8B. Through this processing, clones that become parents in the phylogenetic tree 113 are determined from candidates for parents of individual clones in consideration of correlation coefficients among mutation group frequencies.

At step S1001, the parent-child relation determination section 111 is applied to all clones of the parent-child graph 601. If pieces of processing to all the clones have been finished, the whole processing is finished.

At step S1002, one clone to become a processing target is selected. Hereinafter, this clone will be referred to as a clone v.

At step S1003, it is judged whether there are plural candidates for a parent of the clone v or not. If there is not plural candidates, it is not necessary to select one candidate as the parent, therefore the flow goes back to step S1001 to perform processing on another clone.

At step S1004, variables used at steps S1005 to S1010 are initialized. S is the maximum value for showing the likelihood of the clone v being a parent, and U is a variable for recording a candidate for a parent corresponding to the maximum value.

At step S1005, pieces of processing at steps S1005 to S1009 are applied to all candidates u for a parent of the clone v. If pieces of processing to such all the clones u have already been finished, the flow proceeds to step S1010.

At step S1006, one candidate, which is a candidate for a parent of the clone v and which has not been processed yet, is selected, and it is referred to as a clone u.

At step S1007, a parent candidate score s(u, v) that shows the likelihood of the clone u being a parent of the clone v is calculated. The parent candidate score s(u, v) are given, for example, by the next Expression (1).

$$s(u,v)=e(u,v)+c(u,v)+r(u,v), \quad (1)$$

where e(u, v) is a nonzero value if the expectation that mutations in clones u are also in clone v is backed up by fluorescence hybridization, c(u, v) is a nonzero value if such an expectation is backed up by mutations that co-occur on the same sequence, and r(u, v) is a correlation coefficient among the mutation group frequencies in the plural samples. A clone u that gives the maximum value to the parent candidate score s(u, v) is selected as a parent of the clone v.

The calculation method of the parent candidate score s(u, v) will be explained later with reference to FIG. 11.

At step S1008, it is judged whether the clone u is the first candidate for a parent of the clone v that has ever been processed or not (whether U=an invalid value or not) or whether the score of the clone u is larger than that of any candidate that has already been processed or not (whether s(u, v)>S or not).

At step S1009, when it is judged that the condition at step S1008 is satisfied, S and U are updated.

At step S1010, a clone that gives the maximum score of the likelihood of being a parent of the clone v has been set to U through pieces of processing from step S1005 to step S1009. As for candidates u other than this clone, edges from the candidates u to the clone v are eliminated, therefore only U is a candidate for a parent of the clone v.

The parent-child relation determination section 111 limits a candidate for a parent of each clone to only one. At this moment, the structure of the parent-child graph has become a tree structure. This tree structure is output as a phylogenetic tree 113 as shown in FIG. 8B.

As described above, the parent-child relation determination section 111 calculates a parent candidate score s(u, v) that reflects the likelihood of a clone u being a parent of a clone v about two clones u and v. Hereinafter, the definition of and calculation method of the parent candidate score s(u, v) will be explained.

With regard to a score that reflects the likelihood of a clone being a parent of another clone, it is desirable that mutation co-occurrence data 112, which shows information whether different mutations occur in the same cell or not, should be used. As shown in FIG. 3, the mutation co-occurrence data 112 is data in which judgment whether a pair of mutations (referred to as a mutation pair hereinafter) occurs in the same cell or not as well as the evidence for the judgment is recorded. For example, if the mutation 217 always occurs along with the clone 912, it can be presumed that a clone having the mutation 217 is a child or a descendant of a clone in which the mutation 912 occurred. It is supposed that the evidence for the judgment that a pair of mutations occurs in the same cell is backed up by fluorescence hybridization or information that the pair of mutations exists on the same NGS sequence, but a backup method of the evidence is not limited to the above methods. It desirable that not only a pair of mutations and the evidence but also the reliability of presumption that the mutation pair is in the same cell should be included in mutation co-occurrence data 112. The reliability can be arbitrarily defined on the basis of the number of positions of genomes having a possibility of hybridizing a robe in the case of fluorescence hybridization, and in the case of the reliability being defined on the basis of the same NGS sequence, the reliability can be arbitrarily defined on the basis of the number of positions of genomes on which the sequence may be mapped, or on the basis of the number of NGS sequences including those mutations.

The parent candidate score s(u, v) is given by the above Expression (1).

In Expression (1), e (u, v) is set to a nonzero value if it can be presumed that the mutation of the clone u is inevitably included in a cell having the mutation of the clone v using an experimental means such as fluorescence hybridization, and otherwise it is set to 0. A value obtained by multiplying a parameter E, which is given in advance and recorded in a memory section, by the reliability stored in the mutation co-occurrence data 112 can be used as the nonzero value, for example. If there is information about plural mutation pairs regarding the clones u and v, a general reliability obtained in consideration of all the reliabilities of those pairs (for example, the arithmetic average of all the reliabilities) is used as the nonzero value.

In Expression (1), c(u, v) is set to a nonzero value if there are mutations belonging to u and v respectively on the same NGS sequence, and it can be presumed that the mutation of the clone u is inevitably included in a cell having the mutation of the clone v by referring the sequence, and otherwise it is set to 0. A value obtained by multiplying a parameter C, which is given in advance and recorded in a memory section, by the reliability stored in the mutation co-occurrence data 112 can be used as the nonzero value, for example. If there is information about plural mutation pairs regarding the clones u and v, a general reliability obtained in consideration of all the reliabilities of those pairs (for example, the arithmetic average of all the reliabilities) is used as the nonzero value.

In Expression (1), r(u, v) is a correlation coefficient among the mutation group frequencies corresponding to the clones u and v in the plural samples. If the clone v is a child of the clone u, when the mixture ratio of the clone v increases, it can be thought that there is a tendency of both frequencies of the mutations possessed by the clones u and v being increased. This correlation is taken into consideration by r(u, v).

In addition, the parent candidate score s(u, v) can be easily enhanced by adding a new term to Expression (1) even in the case where it is judged by an evidence other than the fluorescence hybridization and the existence on the same NGS sequence that a pair of mutations is present in the same cell.

Figure 11:
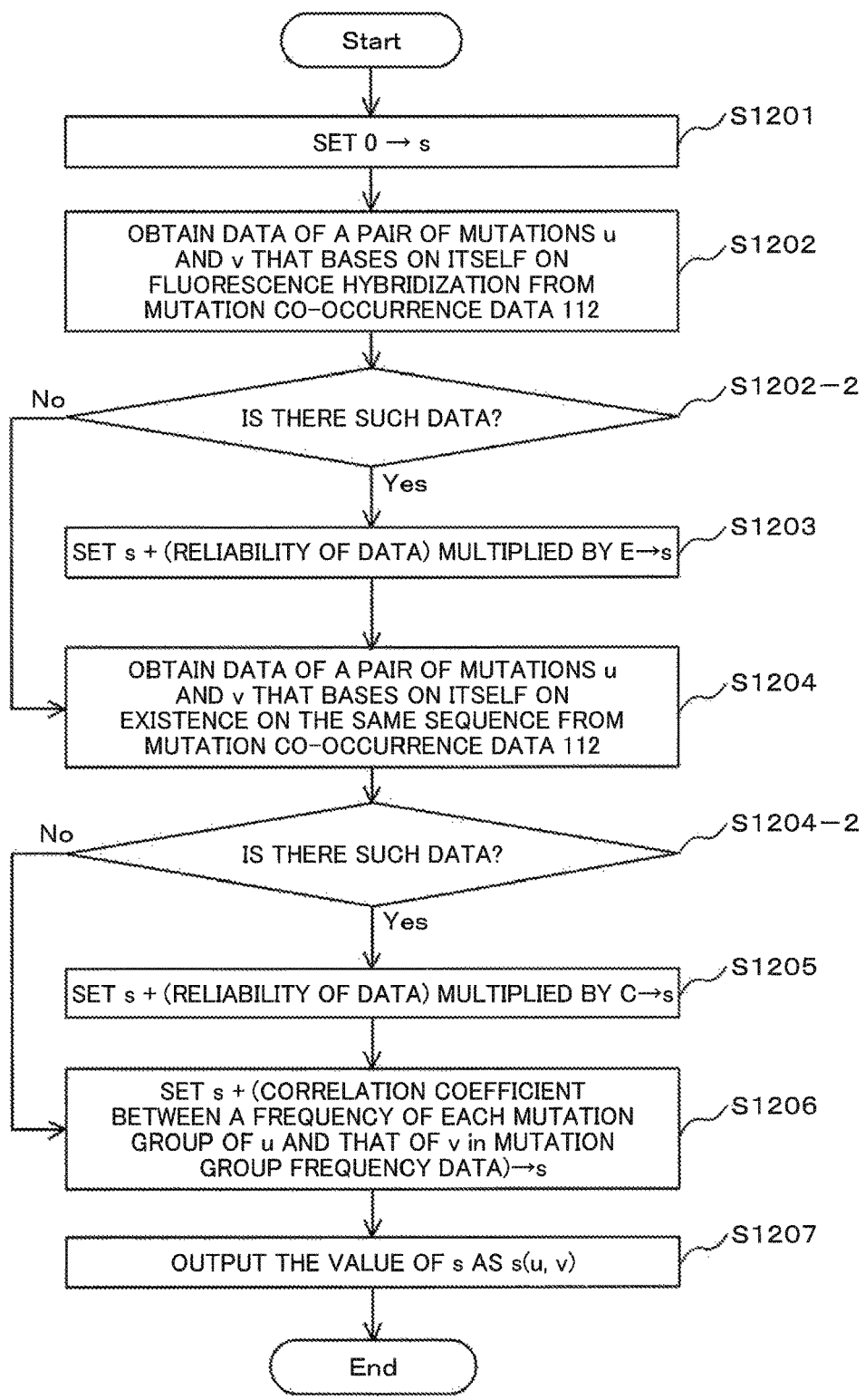
FIG. 11 is a diagram showing the method for calculating a score of the likelihood of a parent-child relation (parent candidate score) between two clones.

FIG. 11 shows a flowchart of processing for calculating a parent candidate score s(u, v).

Hereinafter, the details of the processing for calculating a parent candidate score s(u, v) will be explained with reference to FIG. 11.

At step S1201, a variable s is initialized.

At step S1202, an attempt is made to obtain data of a mutation pair (u, v) that bases itself on fluorescence hybridization from mutation co-occurrence data 112.

At step S1202-2, if there is such data, the flow proceeds to step S1203, and otherwise the flow proceeds to step S1204.

At step S1203, a value obtained by multiplying the value of the parameter E by the reliability of the data is added to s.

At step S1204, an attempt is made to obtain data of the mutation pair (u, v) that bases itself on existence on the same sequence from the mutation co-occurrence data 112.

At step S1204-2, if there is such data, the flow proceeds to step S1205, and otherwise the flow proceeds to step S1206.

At step S1205, a value obtained by multiplying the value of the parameter C by the reliability of the data is added to s.

At step S1206, correlation coefficients among frequencies of individual mutation groups of u and those of v in mutation group frequency data are added to s.

At step S1207, the value of s is output as the parent candidate score s(u, v).

As described above, according to the present invention, even if which mutations are derived from the same cell is unavailable, phylogenetic tree 113 can be created by calculating parent candidate score s(u, v).

In this way, according to this embodiment, using correlations among mixture ratios in plural samples of a cancer, a phylogenetic tree regarding plural clones whose DNA sequences are unavailable can be created with high accuracy and at low cost. In other words, by judging whether edges of a phylogenetic tree should be cut or not from the mixture ratio of a clone and other clones that have evolved from the former clone, it becomes possible that correct evolutionary relations are prevented from being cut off.

Furthermore, by using such high accurate phylogenetic tree, evolutionary relations among clones can be identified with high accuracy.

Figure 13:
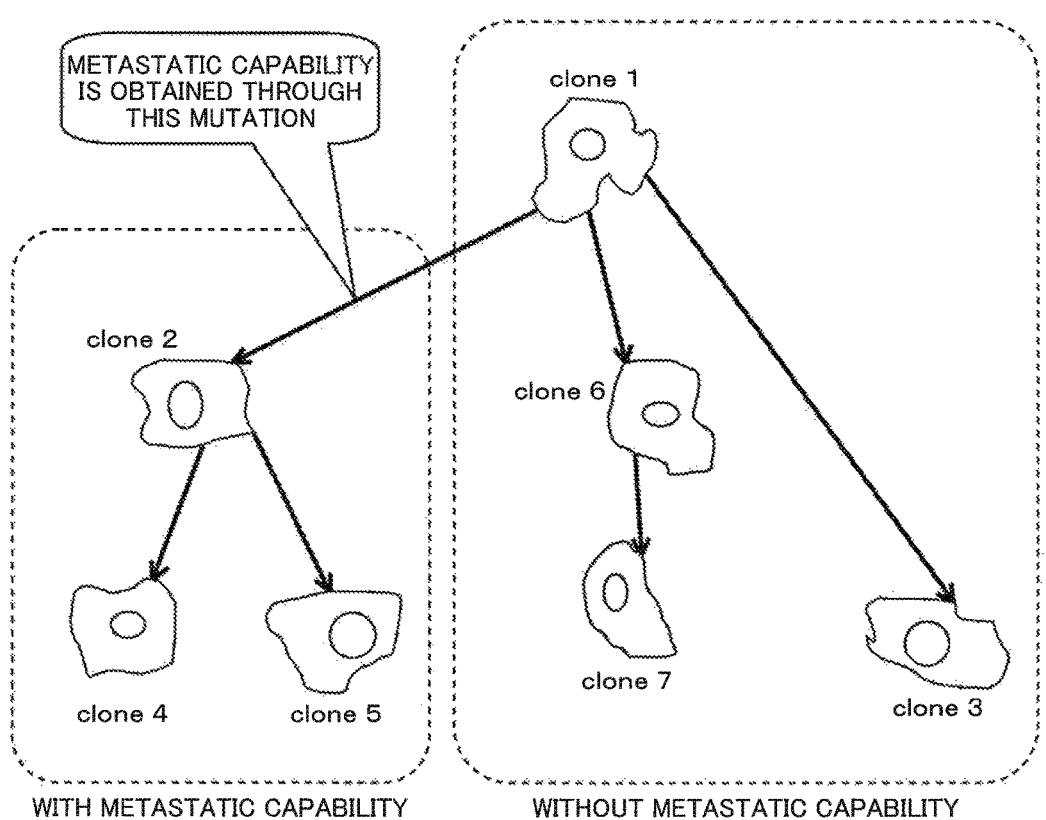
FIG. 13 is a diagram showing an application example of a phylogenetic tree for clones generated in the first embodiment.
Figure 1:
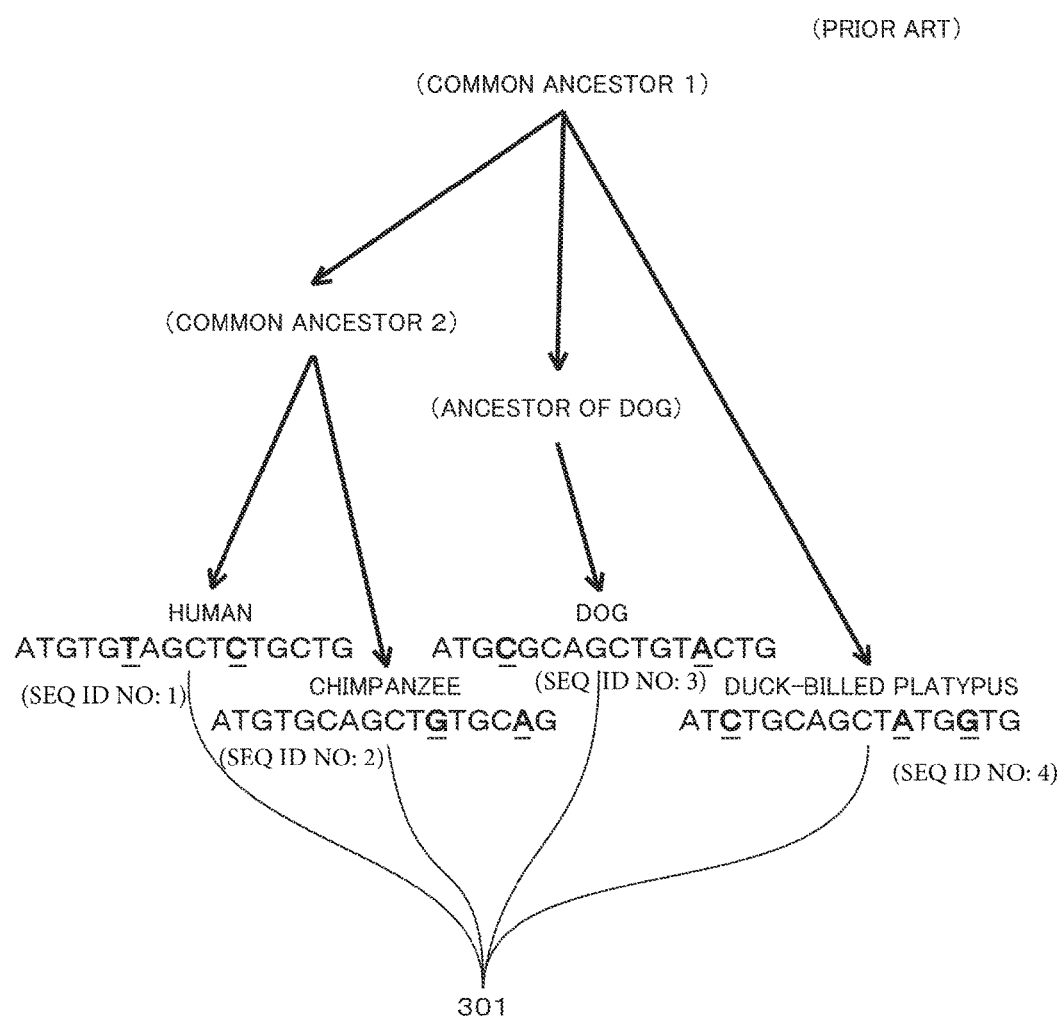

For example, by displaying a phylogenetic tree created from a sample of cancer clones shown in FIG. 13 on the user interface section 106 as an output, a user can presume the occurrence of serious change by which a cancer obtains metastatic capacity took place in mutation from a clone 1 to a clone 2, and can identify the mutation between cells that is important in the progressive process of the cancer as the mutation from the clone 1 to the clone 2. In this way, evolutionary relations among clones, that is to say, changing processes that show in clones where mutations are generated and clones that inherit the mutations from a sample including nonuniform cancer cells that have mutations in different positions of genomes, with the result that an important clue for developing of therapeutic agents for the cancer can be obtained, for example.

As described above, according to the present invention, using correlations among frequency data regarding many mutations detected in samples of a cancer, a phylogenetic tree for clones can be created with high accuracy and at low cost.

Although the above-described embodiment relates to the creation of a phylogenetic tree for cancer clones, there is no intention to limit the present invention to the above concrete configuration. The present invention can be applied to the creation of a phylogenetic tree for plural clones, whose DNA sequences are unavailable, other than cancer cells. In other words, various modifications can be made to the present invention as long as those modifications do not deviate from the gist of the above descriptions.

What is claimed is:

1. A phylogenetic tree creation apparatus comprising:
   a central processing unit;
   a main memory device storing programs executed by the central processing unit and data necessary for execution of the programs by the central processing unit, the main memory device including a graph creation section, a shortcut elimination section, and a parent-child relation determination section;

an auxiliary memory device also recording data necessary for execution of the programs by the central processing unit;

a removable medium memory device also recording data necessary for execution of the programs by the central processing unit; and a user interface unit operating as an input/output device providing an interface with a user, wherein, in a case where there is a plurality of samples each of which contains a mixture of a plurality of clones having different genomes, mutations having about the same frequencies are grouped by the central processing unit into one group to make a plurality of groups, and data listing the frequencies of individual groups is referred to as the mutation group frequency data;

wherein the graph creation section of the main memory device creates a parent-child graph, which is a graph where vertices are set to the clones and edges are set to candidates for parent-child relations on the basis of the mutation group frequency data;

wherein the parent-child relation determination section of the main memory device selects clones to become parents of the clones in consideration of correlation coefficients showing correlations among the mutation group frequencies in the plurality of samples, and creates a phylogenetic tree for the plurality of clones;

wherein the shortcut elimination section of the main memory device removes candidates for parent-child relations that are contradictory to the mutation group frequency data in the parent-child graph, after the graph creation section creates the parent-child relations and before the processing of the parent-child relation determination section is performed; and wherein the phylogenetic tree is output to the user interface unit for identification of evolutionary relations by a user.

2. The phylogenetic tree creation apparatus according to claim 1, wherein the parent-child relation determination section selects pairs of clones corresponding respectively to mutation groups such that the frequency of one group is always equal to or greater than the corresponding frequency of another group in all the plurality of samples as candidates for a parent-child relation of two clones.

3. The phylogenetic tree creation apparatus according to claim 1, wherein, in the case where a plurality of candidates for parent clones in the parent-child relations (u) still remain after the elimination of parent-child relations executed by the shortcut elimination section, the parent-child relation determination section selects a candidate that is most likely a parent among the plurality of the candidates, and creates the phylogenetic tree using the selected candidate.

4. The phylogenetic tree creation apparatus according to claim 1, wherein, the apparatus takes as input the mutation co-occurrence data which contain a judgment whether a pair of mutations in the samples occurs in the same cell or not as well as an evidence and a reliability for the judgment; and wherein the parent-child relation determination section selects the pair of clones as a candidate for the parent-child relation on the basis of the mutation co-occurrence data.

5. The phylogenetic tree creation apparatus according to claim 1, wherein, in order to select a pair of two clones (clones u and v) that is a candidate for the parent-child relation, a parent candidate score s(u, v) that is defined by Expression (1) is calculated in the parent-child relation determination section, $$s(u,v)=e(u,v)+c(u,v)+r(u,v) \qquad (1)$$

wherein e(u, v) is a nonzero value if the parent-child relation of the clones u and v are backed up by fluorescence hybridization, c(u, v) is a nonzero value if the parent-child relation of the clones u and v is backed up by mutations that co-occur on the same sequence, and this can be confirmed, r(u, v) is a correlation coefficient among the mutation group frequencies in the plurality of samples, and wherein, a clone u that gives the maximum value to the parent candidate score is selected as a parent of the clone v.

6. The phylogenetic tree creation apparatus according to claim 5, wherein the phylogenetic tree creation apparatus creates a phylogenetic tree for clones on the basis of samples of a cancer;

inputs mutation co-occurrence data, which is obtained using fluorescence hybridization, from a plurality of samples of tissues including cells of the cancer in order to check the presence or absence of the co-occurrence regarding e(u, v) of Expression (1); and inputs mutation co-occurrence data which is obtained from sequence data obtained using the NGS analysis regarding c(u, v).

7. The phylogenetic tree creation apparatus according to claim 6, further comprising a memory section for storing the mutation group frequency data, the mutation co-occurrence data, and the phylogenetic tree regarding samples of cancer cells such that each of the samples contains a mixture of a plurality of clones having different genomes, wherein the mutation co-occurrence data contains data for confirming the presence or absence of the co-occurrence of the pair of mutations, in which a judgment whether a pair of mutations occurs in the same cell or not as well as the evidence and the reliability for the judgment is recorded.

8. The phylogenetic tree creation apparatus according to claim 7, wherein the nonzero value of e(u, v) in Expression (1) is a value obtained by multiplying a parameter E that is given in advance and recorded in the memory section by the reliability, and in the case where there is information about a plurality of mutations regarding the clones u and v, a general reliability obtained in consideration of all the reliabilities of pieces of information about the plurality of mutation pairs is used as the reliability.

9. The phylogenetic tree creation apparatus according to claim 7, wherein the memory section holds information of NGS sequences obtained from the samples of the cancer cells, and c(u, v) in Expression (1) is set to the nonzero value in the case where there are mutations that belong to u and v on the same NGS sequence, and it can be presumed that the mutation belonging to the clone u is surely included in a cell having the mutation belonging to the clone v by referring to the sequence, and otherwise is set to zero.

10. A system for creating a phylogenetic tree for clones, comprising:

a central processing unit;

a main memory device storing programs executed by the central processing unit and data necessary for execution of the programs by the central processing unit, the main memory device including a graph creation section, a shortcut elimination section, a parent-child relation determination section, and a memory section;

an auxiliary memory device also recording data necessary for execution of the programs by the central processing unit;

a removable medium memory device also recording data necessary for execution of the programs by the central processing unit; and a user interface unit operating as an input/output device providing an interface with a user, wherein, in a case where there is a plurality of samples each of which contains a mixture of a plurality of clones having different genomes, mutations having about the same frequencies are grouped by the central processing unit into one group to make a plurality of groups, and data listing the frequencies of individual groups is referred to as mutation group frequency data;

the graph creation section of the main memory device creates the parent-child graph;

the parent-child relation determination section of the main memory device selects clones to become parents of the individual clones in consideration of correlation coefficients showing correlations among the mutation group frequencies in the plurality of samples, and creates a phylogenetic tree for the plurality of clones;

wherein the shortcut elimination section of the main memory device removes candidates for parent-child relations that are contradictory to the mutation group frequency data in the parent-child graph, after the graph creation section creates the parent-child relations and before the processing of the parent-child relation determination section is performed; and wherein the phylogenetic tree is output to the user interface unit for identification of evolutionary relations by a user.

* * * * *

SEQUENCE LISTING

```
<160> NUMBER OF SEQ ID NOS: 4

<210> SEQ ID NO 1
<211> LENGTH: 16
<212> TYPE: DNA
<213> ORGANISM: Homo sapiens

<400> SEQUENCE: 1
atgtgtagct ctgctg                                                  16

<210> SEQ ID NO 2
<211> LENGTH: 16
<212> TYPE: DNA
<213> ORGANISM: Pan troglodytes

<400> SEQUENCE: 2
atgtgcagct gtgcag                                                  16

<210> SEQ ID NO 3
<211> LENGTH: 16
<212> TYPE: DNA
<213> ORGANISM: Canis familiaris

<400> SEQUENCE: 3
atgcgcagct gtactg                                                  16

<210> SEQ ID NO 4
<211> LENGTH: 16
<212> TYPE: DNA
<213> ORGANISM: Ornithorhynchus anatinus

<400> SEQUENCE: 4
atctgcagct atggtg                                                  16
```